(12) United States Patent
Kim et al.

(10) Patent No.: US 8,647,879 B2
(45) Date of Patent: Feb. 11, 2014

(54) PEPTIDE PROBE FOR RAPID AND SPECIFIC DETECTION OF β-AMYLOID AGGREGATION

(75) Inventors: Jin Ryoun Kim, Jericho, NY (US); Yang Hu, Brooklyn, NY (US); Jorge Ghiso, Elmhurst, NY (US)

(73) Assignee: Polytechnic Institute of NYU, Brooklyn, NY (US)

( * ) Notice: Subject to any disclaimer, the term of this patent is extended or adjusted under 35 U.S.C. 154(b) by 0 days.

(21) Appl. No.: 12/856,209

(22) Filed: Aug. 13, 2010

(65) Prior Publication Data

US 2012/0009685 A1    Jan. 12, 2012

Related U.S. Application Data

(60) Provisional application No. 61/234,083, filed on Aug. 14, 2009.

(51) Int. Cl.
*G01N 21/64* (2006.01)
*G01N 1/38* (2006.01)

(52) U.S. Cl.
USPC .............. 436/86; 436/172; 436/174; 436/179

(58) Field of Classification Search
None
See application file for complete search history.

(56) References Cited

PUBLICATIONS

Fulop, L. et al. "Synthesis and Fluorescent Labeling of Beta-Amyloid Peptides," J. Peptide Sci. 7: 397-401 (2001).*
Garai K. et al. "Detecting Amyloid-beta Aggregation with Fiber-Based Fluorescence Correlation Spectroscopy," Biophysical Journal: Biophysical Letters 92, 2007, L55-L57.*

* cited by examiner

*Primary Examiner* — Yelena G Gakh
*Assistant Examiner* — Michelle Adams
(74) *Attorney, Agent, or Firm* — Laurence P. Colton; Smith Risley Tempel Santos LLC

(57) ABSTRACT

A peptide probe that generates fluorescence signals rapidly upon recognition of various Aβ aggregates without significant perturbation of samples. The present peptide probes display an increase in fluorescence signals upon coincubation with Aβ oligomers, but neither monomeric/dimeric species nor fibrils. The detection can occur within an hour or two without any additional sample preparation and incubation steps.

24 Claims, 6 Drawing Sheets

PEPTIDE PROBE FOR RAPID AND SPECIFIC DETECTION OF β-AMYLOID AGGREGATION

STATEMENT OF RELATED APPLICATIONS

This application is based on and claims the benefit of U.S. Provisional Patent Application No. 61/234,083 having a filing date of 14 Aug. 2010, which is incorporated herein in its entirety by this reference.

SEQUENCE LISTING

The instant application contains a Sequence Listing which has been submitted in ASCII format via EFS-Web and is hereby incorporated by reference in its entirety. Said ASCII copy, created on Sep. 16, 2011, is named 484673US.txt and is 2,831 bytes in size.

BACKGROUND OF THE INVENTION

1. Technical Field

This invention is generally related to the field of peptide probes, to the field of peptide probes for the detection of amyloid aggregation, and to the field of peptide probes for the rapid and specific detection of amyloid aggregation.

2. Prior Art

Aggregation of a 39-43 amino acid peptide, beta amyloid (Aβ) (Kang, J., et al., The precursor of Alzheimer's disease amyloid A4 protein resembles a cell-surface receptor, *Nature* 325, 733-736, 1987; Roher, A. E., et al., beta-Amyloid-(1-42) is a major component of cerebrovascular amyloid deposits: implications for the pathology of Alzheimer disease, *Proc Natl Acad Sci USA* 90, 10836-10840, 1993), into a fibril via formation of nuclei (Kusumoto, Y., et al., Temperature dependence of amyloid beta-protein fibrillization, *Proc Natl Acad Sci USA* 95, 12277-12282, 1998; Teplow, D. B., et al., Elucidating amyloid beta-protein folding and assembly: A multidisciplinary approach, *Acc Chem Res* 39, 635-645, 2006; Fernandez-Busquets, X., et al., Recent structural and computational insights into conformational diseases, *Curr Med Chem* 15, 1336-1349, 2008; Lazo, N. D., et al., On the nucleation of amyloid beta-protein monomer folding, *Protein Sci* 14, 1581-1596, 2005; Wetzel, R., et al., Plasticity of amyloid fibrils. *Biochemistry* 46, 1-10, 2007) is believed to be implicated in the pathology of Alzheimer's disease (AD), which is a neurodegenerative disorder characterized by a progressive loss of cognitive functions and by neuropathological features comprising amyloid deposits and neuronal losses in the brain (Hardy, J., et al., The amyloid hypothesis of Alzheimer's disease: progress and problems on the road to therapeutics, *Science* 297, 353-356, 2002; Mattson, M. P., Pathways towards and away from Alzheimer's disease, *Nature* 430, 631-639, 2004; Haass, C., et al., Soluble protein oligomers in neurodegeneration: lessons from the Alzheimer's amyloid beta-peptide, *Nat Rev Mol Cell Biol* 8, 101-112, 2007).

Low molecular weight Aβ species, such as monomers and dimmers, are not toxic (Haass, C., et al., (2007) Soluble protein oligomers in neurodegeneration: lessons from the Alzheimer's amyloid beta-peptide, *Nat Rev Mol Cell Biol* 8, 101-112, 2007; Kayed, R., et al., Common structure of soluble amyloid oligomers implies common mechanism of pathogenesis, *Science* 300, 486-489, 2003; Kayed, R., et al., Permeabilization of lipid bilayers is a common conformation-dependent activity of soluble amyloid oligomers in protein misfolding diseases, *J Biol Chem* 279, 46363-46366, 2004; Klyubin, I., et al., Amyloid beta protein immunotherapy neutralizes Abeta oligomers that disrupt synaptic plasticity in vivo, *Nat Med* 11, 556-561, 2005). A considerable amount of data has identified the soluble Aβ oligomers as potentially significant toxic agents (Haass, C., et al., Soluble protein oligomers in neurodegeneration: lessons from the Alzheimer's amyloid beta-peptide, *Nat Rev Mol Cell Biol* 8, 101-112, 2007; Glabe, C. G., Common mechanisms of amyloid oligomer pathogenesis in degenerative disease, *Neurobiol Aging* 27, 570-575, 2006). However, the possibility that the AR fibrils may be associated with neurotoxicity cannot be ruled out, since fibrillar aggregates can serve as a pool of soluble intermediate species through a dynamic exchange with monomers or oligomers (Id.; O'Nuallain, B., et al., Thermodynamics of A beta(1-40) amyloid fibril elongation, *Biochemistry* 44, 12709-12718, 2005; Martins, I. C., et al., Lipids revert inert Abeta amyloid fibrils to neurotoxic protofibrils that affect learning in mice, *EMBO J* 27, 224-233, 2008). Toxic oligomers are kinetic intermediates, and can display changes in conformation and toxic effects by subtle environmental changes (Teplow, D. B., et al., Elucidating amyloid beta-protein folding and assembly: A multidisciplinary approach, *Acc Chem Res* 39, 635-645, 2006; Wetzel, R., et al., Plasticity of amyloid fibrils, *Biochemistry* 46, 1-10, 2007; Haass, C., et al., Soluble protein oligomers in neurodegeneration: lessons from the Alzheimer's amyloid beta-peptide, *Nat Rev Mol Cell Biol* 8, 101-112, 2007; Klyubin, I., et al., Amyloid beta protein immunotherapy neutralizes Abeta oligomers that disrupt synaptic plasticity in vivo, *Nat Med* 11, 556-561, 2005).

Determination of population profiles of different aggregate species is strongly required to understand the molecular causes of Aβ aggregation as well as toxic processes in AD. However, the complex nature of Aβ aggregation, including the generation of transient aggregate intermediates, impedes the establishment of a functional correlation between AR aggregation characteristics and their cellular/clinical manifestations. A quantitative measurement of aggregate species must be done rapidly without significant perturbation of samples for high level accuracy, as aggregates including toxic soluble oligomers are likely to undergo further structural changes during the additional sample preparation and incubation steps (Haass, C., et al., Soluble protein oligomers in neurodegeneration: lessons from the Alzheimer's amyloid beta-peptide, *Nat Rev Mol Cell Biol* 8, 101-112, 2007; Chromy, B. A., et al., Self-assembly of Abeta(1-42) into globular neurotoxins. *Biochemistry* 42, 12749-12760, 2003; Hoyer, W., et al., Dependence of alpha-synuclein aggregate morphology on solution conditions, *J Mol Biol* 322, 383-393, 2002). Rapid and specific detection of distinct amyloidogenic species is therefore quintessential for the establishment of a reliable correlation between aggregation profiles and their cellular/clinical manifestations as well as achieving better understanding of the determinants of aggregation.

Inaccurate quantification of various aggregate species would result in the gap seen between basic scientific discovery and cellular/clinical manifestations, and the discrepancy among observations from animal model studies. The currently available compounds or methods, however, either do not distinguish different aggregate species or are inappropriate for rapid, non-perturbative detection due to the requirement of additional sample preparation and incubation steps (Kayed, R., et al., Common structure of soluble amyloid oligomers implies common mechanism of pathogenesis, *Science* 300, 486-489, 2003; Williams, A. D., et al., Structural properties of Abeta protofibrils stabilized by a small molecule, *Proc Natl Acad Sci USA* 102, 7115-7120, 2005; Kayed, R., et al., Conformation-dependent anti-amyloid oligomer antibodies, *Methods Enzymol* 413, 326-344, 2006; Kayed, R., et al., Fibril specific, conformation dependent antibodies recognize a generic epitope common to amyloid fibrils and fibrillar oligomers that is absent in prefibrillar oligomers, *Mol Neurodegener* 2, 18, 2007; Linke, R. P., et al., High-sensitivity diagnosis of AA amyloidosis using Congo red and immunohistochemistry detects missed amyloid deposits, *J Histochem Cytochem* 43, 863-869, 1995; LeVine, H., 3rd, Quantification of beta-sheet amyloid fibril structures with thioflavin T, *Methods Enzymol* 309, 274-284, 1999).

Accordingly, there is always a need for improved probes for the detection of amyloid aggregation. There also always is a need for improved peptide probes for the rapid and specific detection of amyloid aggregation. It is to these needs, among others, that this invention is directed.

BRIEF SUMMARY OF THE INVENTION

Determination of population profiles of different aggregate species is strongly required to understand the molecular causes of beta-amyloid (Aβ) aggregation as well as toxic processes in Alzheimer's disease (AD). A quantitative measurement of aggregate species must be done rapidly without perturbation of samples for high level accuracy, as aggregates including toxic soluble oligomers are likely to undergo further structural changes during the additional sample preparation and incubation steps. The present invention is a design of a peptide probe that may generate fluorescence signals rapidly upon recognition of various Aβ aggregates without significant perturbation of samples. The present peptide probe displays an increase in fluorescence signals upon coincubation with AR oligomers, but neither monomeric/dimeric species nor fibrils. The detection can occur within an hour or two without any additional sample preparation and incubation steps.

The peptide probe can be used for detection of toxic Aβ oligomers for diagnostic applications of Alzheimer's disease on tissue samples or biological fluids, for screening of therapeutic agents that can alter the protein aggregation process and the resulting aggregate toxicity, and provides a sensitive and specific assay for Aβ aggregate formation in biochemical studies.

These uses and features, and other uses, features and advantages of the present invention, will become more apparent to those of ordinary skill in the relevant art when the following detailed description of the preferred embodiments is read in conjunction with the appended figures.

DETAILED DESCRIPTION OF PREFERRED EMBODIMENTS

Figure 1:
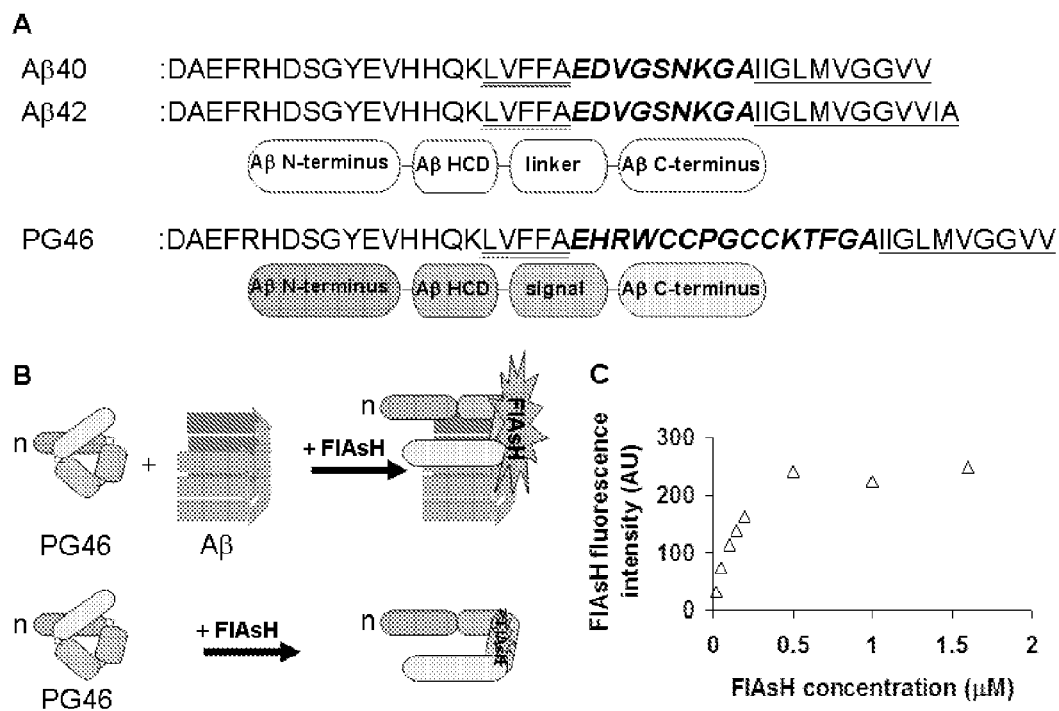
FIG. 1A is the amino acid sequences of Aβ40, Aβ42 and PG46. The Aβ N-terminal domain is shown in plain letters. The Aβ HCD domain is double underlined. The Aβ C-terminal domain is single underlined. The linker region in Aβ40 and Aβ42, and the signal domain in PG46 are shown in bold italic letters.
FIG. 1B is the proposed mechanism of modulation of FlAsH fluorescence of PG46 through association with Aβ oligomers.
FIG. 1C is the FlAsH-concentration dependent FlAsH fluorescence of PG46. The concentration of PG46 was 0.05 mg/ml. The excitation wavelength was 508 nm.

Alzheimer's disease (AD) is a neurodegenerative disorder characterized by a progressive loss of cognitive functions and by neuropathological features comprising amyloid deposits and neuronal losses in brain (Hardy, J., et al., The amyloid hypothesis of Alzheimer's disease: progress and problems on the road to therapeutics, Science 297, 353-356, 2002; Mattson, M. P., Pathways towards and away from Alzheimer's disease, Nature 430, 631-639 (2004). The principal constituent of amyloid deposits is a 40-42 amino acid peptide, referred to as β amyloid (Aβ) (FIG. 1A) (Kang, J., et al., The precursor of Alzheimer's disease amyloid A4 protein resembles a cell-surface receptor, Nature 325, 733-736, 1987; Roher, A. E., et al., beta-Amyloid-(1-42) is a major component of cerebrovascular amyloid deposits: implications for the pathology of Alzheimer disease, Proc Natl Acad Sci USA 90, 10836-10840, 1993). Aβ is derived from the amyloid precursor protein (APP) by proteolytic cleavage[1] (Kang, J., et al., The precursor of Alzheimer's disease amyloid A4 protein resembles a cell-surface receptor, Nature 325, 733-736, 1987). Aβ contains the hydrophilic N-terminus (D1-K16), the hydrophobic central domain (HCD, L17-A21), the linker region (E22-A30), and the hydrophobic C-terminus (I31-V40 or I31-A42 in Aβ40 and Aβ42, respectively) (FIG. 1A) (Id.). Whereas the N-terminus is not essential in aggregation (Pike, C. J., et al., Amino-terminal deletions enhance aggregation of beta-amyloid peptides in vitro, J Biol Chem 270, 23895-23898, 1995), HCD and the C-terminus of Aβ have been found to be critical in Aβ self-assembly and aggregation-prone (Tjernberg, L. O., et al., Arrest of beta-amyloid fibril formation by a pentapeptide ligand, J Biol Chem 271, 8545-8548, 1996; Soto, C., et al., Beta-sheet breaker peptides inhibit fibrillogenesis in a rat brain model of amyloidosis: implications for Alzheimer's therapy, Nat Med 4, 822-826, 1998; Liu, R., et al., Residues 17-20 and 30-35 of beta-amyloid play critical roles in aggregation, J Neurosci Res 75, 162-171, 2004; Christopeit, T., et al., Mutagenic analysis of the nucleation propensity of oxidized Alzheimer's beta-amyloid peptide, Protein Sci 14, 2125-2131, 2005). Aggregation of Aβ into fibrils via formation of nuclei is believed to be implicated in the pathology of AD (Kusumoto, Y., et al., Temperature dependence of amyloid beta-protein fibrillization, Proc Natl Acad Sci USA 95, 12277-12282, 1998; Teplow, D. B., et al., Elucidating amyloid beta-protein folding and assembly: A multidisciplinary approach, Acc Chem Res 39, 635-645, 2006; Fernandez-Busquets, X., et al., Recent structural and computational insights into conformational diseases, Curr Med Chem 15, 1336-1349, 2008; Lazo, N. D., et al., On the nucleation of amyloid beta-protein monomer folding, Protein Sci 14, 1581-1596, 2005; Wetzel, R., et al., Plasticity of amyloid fibrils, Biochemistry 46, 1-10, 2007; Hardy, J., et al., The amyloid hypothesis of Alzheimer's disease: progress and problems on the road to therapeutics, Science 297, 353-356, 2002; Mattson, M. P., Pathways towards and away from Alzheimer's disease, Nature 430, 631-639, 2004; Haass, C. et al., Soluble protein oligomers in neurodegeneration: lessons from the Alzheimer's amyloid beta-peptide, Nat Rev Mol Cell Biol 8, 101-112, 2007).

Experimental and simulation studies have suggested that conformational rearrangement of Aβ occurs during the assembly of monomers into oligomers, then into fibrils (Teplow, D. B., et al., Elucidating amyloid beta-protein folding and assembly: A multidisciplinary approach, Acc Chem Res 39, 635-645, 2006; Fernandez-Busquets, X., et al., Recent structural and computational insights into conformational diseases, Curr Med Chem 15, 1336-1349, 2008; Lazo, N. D., et al., On the nucleation of amyloid beta-protein monomer folding, Protein Sci 14, 1581-1596, 2005; Wetzel, R., et al., Plasticity of amyloid fibrils, Biochemistry 46, 1-10, 2007). Monomeric Aβ is, in large, irregularly structured (Zhang, S., et al., The Alzheimer's peptide a beta adopts a collapsed coil structure in water, J Struct Biol 130, 130-141, 2000; Lee, J. P., et al., 1H NMR of A beta amyloid peptide congeners in water solution, Conformational changes correlate with plaque competence, Biochemistry 34, 5191-5200, 1995; Riek, R., et al., NMR studies in aqueous solution fail to identify significant conformational differences between the monomeric forms of two Alzheimer peptides with widely different plaque-competence, A beta(1-40)(ox) and A beta(1-42)(ox), Eur J Biochem 268, 5930-5936, 2001; Hou, L., et al., Solution NMR studies of the A beta(1-40) and A beta(1-42) peptides establish that the Met35 oxidation state affects the mechanism of amyloid formation, J Am Chem Soc 126, 1992-2005, 2004). Various oligomeric species of Aβ were observed during its aggregation from monomeric states in vivo and in vitro (Klyubin, I., et al., Amyloid beta protein immunotherapy neutralizes Abeta oligomers that disrupt synaptic plasticity in vivo, Nat Med 11, 556-561, 2005; Goldsbury, C., et al., Multiple assembly pathways underlie amyloid-beta fibril polymorphisms, J Mol Biol 352, 282-298, 2005; Harper, J. D., et al., Observation of metastable Abeta amyloid protofibrils by atomic force microscopy, Chem Biol 4, 119-125, 1997; Lansbury, P. T., Jr., Evolution of amyloid: what normal protein folding may tell us about fibrillogenesis and disease, Proc Natl Acad Sci USA 96, 3342-3344, 1999; Walsh, D. M., et al., Amyloid beta-protein fibrillogenesis. Structure and biological activity of protofibrillar intermediates, J Biol Chem 274, 25945-25952, 1999; Huang, T. H., et al., Structural studies of soluble oligomers of the Alzheimer beta-amyloid peptide, J Mol Biol 297, 73-87, 2000; Nichols, M. R., et al., Growth of beta-amyloid(1-40) protofibrils by monomer elongation and lateral association. Characterization of distinct products by light scattering and atomic force microscopy, Biochemistry 41, 6115-6127, 2002; Yong, W., et al., Structure determination of micelle-like intermediates in amyloid beta-protein fibril assembly by using small angle neutron scattering, Proc Natl Acad Sci USA 99, 150-154, 2002; Hoshi, M., et al., Spherical aggregates of beta-amyloid (amylospheroid) show high neurotoxicity and activate tau protein kinase l/glycogen synthase kinase-3beta, Proc Natl Acad Sci USA 100, 6370-6375, 2003; Barghorn, S., et al., Globular amyloid beta-peptide oligomer—a homogenous and stable neuropathological protein in Alzheimer's disease, J Neurochem 95, 834-847, 2005; Chimon, S., et al., Capturing intermediate structures of Alzheimer's beta-amyloid, Abeta (1-40), by solid-state NMR spectroscopy, J Am Chem Soc 127, 13472-13473, 2005; Chimon, S., et al., Evidence of fibril-like beta-sheet structures in a neurotoxic amyloid intermediate of Alzheimer's beta-amyloid, Nat Struct Mol Biol, 2007; Hepler, R. W., et al., Solution state characterization of amyloid beta-derived diffusible ligands, Biochemistry 45, 15157-15167, 2006; Losic, D., et al., High resolution scanning tunnelling microscopy of the beta-amyloid protein (Abeta1-40) of Alzheimer's disease suggests a novel mechanism of oligomer assembly, J Struct Biol 155, 104-110, 2006; Mastrangelo, I. A., et al., High-resolution atomic force microscopy of soluble Abeta42 oligomers, J Mol Biol 358, 106-119, 2006; Walsh, D. M., et al., Naturally secreted oligomers of amyloid beta protein potently inhibit hippocampal long-term potentiation in vivo, *Nature* 416, 535-539, 2002; Podlisny, M. B., et al., Aggregation of secreted amyloid beta-protein into sodium dodecyl sulfate-stable oligomers in cell culture, *J Biol Chem* 270, 9564-9570, 1995; Walsh, D. M., et al., The oligomerization of amyloid beta-protein begins intracellularly in cells derived from human brain, *Biochemistry* 39, 10831-10839, 2000; Lesne, S., et al., A specific amyloid-beta protein assembly in the brain impairs memory, *Nature* 440, 352-357, 2006). Several Aβ oligomers, such as spherical and protofibrillar species, were proposed as the structural units from which larger aggregates emerge (Goldsbury, C., et al., Multiple assembly pathways underlie amyloid-beta fibril polymorphisms, *J Mol Biol* 352, 282-298, 2005; Harper, J. D., et al., Observation of metastable Abeta amyloid protofibrils by atomic force microscopy, *Chem Biol* 4, 119-125, 1997; Lansbury, P. T., Jr., Evolution of amyloid: what normal protein folding may tell us about fibrillogenesis and disease, *Proc Natl Acad Sci USA* 96, 3342-3344, 1999; Walsh, D. M., et al., Amyloid beta-protein fibrillogenesis. Structure and biological activity of protofibrillar intermediates, *J Biol Chem* 274, 25945-25952, 1999; Huang, T. H., et al., Structural studies of soluble oligomers of the Alzheimer beta-amyloid peptide, *J Mol Biol* 297, 73-87, 2000; Nichols, M. R., et al., Growth of beta-amyloid(1-40) protofibrils by monomer elongation and lateral association. Characterization of distinct products by light scattering and atomic force microscopy, *Biochemistry* 41, 6115-6127, 2002; Yong, W., et al., Structure determination of micelle-like intermediates in amyloid beta-protein fibril assembly by using small angle neutron scattering, *Proc Natl Acad Sci USA* 99, 150-154, 2002; Hoshi, M., et al., Spherical aggregates of beta-amyloid (amylospheroid) show high neurotoxicity and activate tau protein kinase I/glycogen synthase kinase-3beta, *Proc Natl Acad Sci USA* 100, 6370-6375, 2003; Barghorn, S., et al., Globular amyloid beta-peptide oligomer—a homogenous and stable neuropathological protein in Alzheimer's disease, *J Neurochem* 95, 834-847, 2005; Chimon, S., et al., Capturing intermediate structures of Alzheimer's beta-amyloid, Abeta(1-40), by solid-state NMR spectroscopy, *J Am Chem Soc* 127, 13472-13473, 2005; Chimon, S., et al., Evidence of fibril-like beta-sheet structures in a neurotoxic amyloid intermediate of Alzheimer's beta-amyloid, *Nat Struct Mol Biol,* 2007; Hepler, R. W., et al., Solution state characterization of amyloid beta-derived diffusible ligands, *Biochemistry* 45, 15157-15167, 2006; Losic, D., et al., High resolution scanning tunnelling microscopy of the beta-amyloid protein (Abeta1-40) of Alzheimer's disease suggests a novel mechanism of oligomer assembly, *J Struct Biol* 155, 104-110, 2006; Mastrangelo, I. A., et al., High-resolution atomic force microscopy of soluble Abeta42 oligomers. *J Mol Biol* 358, 106-119, 2006). These oligomers displayed substantial β strand structures (Lansbury, P. T., Jr., Evolution of amyloid: what normal protein folding may tell us about fibrillogenesis and disease, *Proc Natl Acad Sci USA* 96, 3342-3344, 1999; Walsh, D. M., et al., Amyloid beta-protein fibrillogenesis. Structure and biological activity of protofibrillar intermediates, *J Biol Chem* 274, 25945-25952, 1999; Huang, T. H., et al., Structural studies of soluble oligomers of the Alzheimer beta-amyloid peptide, *J Mol Biol* 297, 73-87, 2000; Nichols, M. R., et al., Growth of beta-amyloid (1-40) protofibrils by monomer elongation and lateral association, Characterization of distinct products by light scattering and atomic force microscopy, *Biochemistry* 41, 6115-6127, 2002; Barghorn, S., et al., Globular amyloid beta-peptide oligomer—a homogenous and stable neuropathological protein in Alzheimer's disease, *J Neurochem* 95, 834-847, 2005; Chimon, S., et al., Capturing intermediate structures of Alzheimer's beta-amyloid, Abeta(1-40), by solid-state NMR spectroscopy, *J Am Chem Soc* 127, 13472-13473, 2005; Chimon, S., et al., Evidence of fibril-like beta-sheet structures in a neurotoxic amyloid intermediate of Alzheimer's beta-amyloid, *Nat Struct Mol Biol,* 2007; Losic, D., et al., High resolution scanning tunnelling microscopy of the beta-amyloid protein (Abeta1-40) of Alzheimer's disease suggests a novel mechanism of oligomer assembly, *J Struct Biol* 155, 104-110, 2006; Mastrangelo, I. A., et al., High-resolution atomic force microscopy of soluble Abeta42 oligomers. *J Mol Biol* 358, 106-119, 2006). Protofibrils of Aβ, curvilinear structures which appeared as strings of the spherical particles in atomic force microscopy (AFM) images, can further grow into fibrils by association with monomers or other protofibrils (Lansbury, P. T., Jr., Evolution of amyloid: what normal protein folding may tell us about fibrillogenesis and disease, *Proc Natl Acad Sci USA* 96, 3342-3344, 1999; Walsh, D. M., et al., Amyloid beta-protein fibrillogenesis. Structure and biological activity of protofibrillar intermediates, *J Biol Chem* 274, 25945-25952, 1999; Huang, T. H., et al., Structural studies of soluble oligomers of the Alzheimer beta-amyloid peptide, *J Mol Biol* 297, 73-87, 2000; Nichols, M. R., et al., Growth of beta-amyloid(1-40) protofibrils by monomer elongation and lateral association, Characterization of distinct products by light scattering and atomic force microscopy, *Biochemistry* 41, 6115-6127, 2002; Losic, D., et al., High resolution scanning tunnelling microscopy of the beta-amyloid protein (Abeta1-40) of Alzheimer's disease suggests a novel mechanism of oligomer assembly, *J Struct Biol* 155, 104-110, 2006; Mastrangelo, I. A., et al., High-resolution atomic force microscopy of soluble Abeta42 oligomers. *J Mol Biol* 358, 106-119, 2006). Soluble oligomers may form β strand-turn-β strand or β strand-loop-β strand structures where the turn or loop may be found within the linker region (Barghorn, S., et al., Globular amyloid beta-peptide oligomer—a homogenous and stable neuropathological protein in Alzheimer's disease, *J Neurochem* 95, 834-847, 2005; Chimon, S., et al., Evidence of fibril-like beta-sheet structures in a neurotoxic amyloid intermediate of Alzheimer's beta-amyloid, *Nat Struct Mol Biol,* 2007; Losic, D., et al., High resolution scanning tunnelling microscopy of the beta-amyloid protein (Abeta1-40) of Alzheimer's disease suggests a novel mechanism of oligomer assembly, *J Struct Biol* 155, 104-110, 2006; Lazo, N. D., et al., On the nucleation of amyloid beta-protein monomer folding, *Protein Sci* 14, 1581-1596, 2005; Hoyer, W., et al., Stabilization of a beta-hairpin in monomeric Alzheimer's amyloid-beta peptide inhibits amyloid formation. *Proc Natl Acad Sci USA* 105, 5099-5104, 2008; Habicht, G., et al., Directed selection of a conformational antibody domain that prevents mature amyloid fibril formation by stabilizing Abeta protofibrils. *Proc Natl Acad Sci USA* 104, 19232-19237, 2007). Amyloid fibrils contain in-register cross β sheets running perpendicular to the long axis of fibrils. Solid state NMR has been successfully used for determination of AR fibril structures (Petkova, A. T., et al., A structural model for Alzheimer's beta-amyloid fibrils based on experimental constraints from solid state NMR, *Proc Natl Acad Sci USA* 99, 16742-16747, 2002; Luhrs, T., et al., 3D structure of Alzheimer's amyloid-beta(1-42) fibrils, *Proc Natl Acad Sci USA* 102, 17342-17347, 2005).

In an Aβ40 fibril model structure, residues D1-E11 of Aβ40 are structurally disordered while the rest of the sequence forms a β strand-loop-β strand motif. β strands are populated within residues V12-V24 and A30-V40, and held together by intermolecular hydrogen bonding parallel to the fibril long axis. A loop structure is formed within residues G25-G29. Consistent with this model, hydrogen-deuterium (HD) exchange studies of Aβ40 fibrils indicated the presence of protected core structures within K16-V36 with rapidly exchangeable amide protons at G25 and S26 (Whittemore, N. A., et al., Hydrogen-deuterium (H/D) exchange mapping of Abeta 1-40 amyloid fibril secondary structure using nuclear magnetic resonance spectroscopy, *Biochemistry* 44, 4434-4441, 2005). The formation of this loop is mediated by cross-strand side chain interactions and a salt bridge between D23 and K28 (Petkova, A. T., et al., A structural model for Alzheimer's beta-amyloid fibrils based on experimental constraints from solid state NMR, *Proc Natl Acad Sci USA* 99, 16742-16747, 2002). This fibril model is largely consistent with Aβ40 fibril structures suggested from alanine and proline scanning mutagenesis analyses, except for the presence of two turns located at E22-D23 and G29-A30 (Williams, A. D., et al., Alanine scanning mutagenesis of Abeta(1-40) amyloid fibril stability, *J Mol Biol* 357, 1283-1294, 2006; Williams, A. D., et al., Mapping abeta amyloid fibril secondary structure using scanning proline mutagenesis, *J Mol Biol* 335, 833-842, 2004).

A fibril structure of Aβ42 with a methionine sulfoxide at position 35 proposed by the Riek group is similar to those of Aβ40 fibrils (Luhrs, T., et al., 3D structure of Alzheimer's amyloid-beta(1-42) fibrils, *Proc Natl Acad Sci USA* 102, 17342-17347, 2005). In an Aβ42 fibril structure model, residues D1-L17 are disordered. The residues V18-S26 and I31-A42 form in-register parallel β sheets mediated by intermolecular hydrogen bonding and stabilized by salt bridge between D23 and K28. The two β strands are connected through the loop region residues N27-A30. Electron paramagnetic resonance spectroscopy studies of Aβ40 and Aβ42 fibrils suggested the presence of a bend-like structure in the residues D23-S26 (Torok, M., et al., Structural and dynamic features of Alzheimer's Abeta peptide in amyloid fibrils studied by site-directed spin labeling, *J Biol Chem* 277, 40810-40815, 2002). Overall, Aβ fibrils display β strand-loop-β strand structures with the loop formed in the linker region.

Recent biophysical and biochemical characterizations have further supported the presence of structural rearrangements, particularly in the region E22-A30 (referred to as the linker region herein), during Aβ aggregation from monomers to fibrils via oligomeric intermediates (Lazo, N. D., et al., On the nucleation of amyloid beta-protein monomer folding, *Protein Sci* 14, 1581-1596, 2005; Grant, M. A., et al., Familial Alzheimer's disease mutations alter the stability of the amyloid beta-protein monomer folding nucleus, *Proc Natl Acad Sci USA* 104, 16522-16527, 2007; Baumketner, A., et al., Amyloid beta-protein monomer structure: a computational and experimental study, *Protein Sci* 15, 420-428, 2006; Baumketner, A., et al., The structure of the Alzheimer amyloid beta 10-35 peptide probed through replica-exchange molecular dynamics simulations in explicit solvent, *J Mol Biol* 366, 275-285, 2007; Triguero, L., et al., Molecular dynamics study to investigate the effect of chemical substitutions of methionine 35 on the secondary structure of the amyloid beta (Abeta(1-42)) monomer in aqueous solution, *J Phys Chem B* 112, 2159-2167, 2008; Borreguero, J. M., et al., Folding events in the 21-30 region of amyloid beta-protein (Abeta) studied in silico, *Proc Natl Acad Sci USA* 102, 6015-6020, 2005). Aβ monomer folding to form a turn conformation in the linker region has been postulated to be an intramolecular nucleation event based on the experimental and theoretical results (Lazo, N. D., et al., On the nucleation of amyloid beta-protein monomer folding, *Protein Sci* 14, 1581-1596, 2005; Grant, M. A., et al., Familial Alzheimer's disease mutations alter the stability of the amyloid beta-protein monomer folding nucleus, *Proc Natl Acad Sci USA* 104, 16522-16527, 2007; Baumketner, A., et al., Amyloid beta-protein monomer structure: a computational and experimental study, *Protein Sci* 15, 420-428, 2006; Baumketner, A., et al., The structure of the Alzheimer amyloid beta 10-35 peptide probed through replica-exchange molecular dynamics simulations in explicit solvent, *J Mol Biol* 366, 275-285, 2007; Triguero, L., et al., Molecular dynamics study to investigate the effect of chemical substitutions of methionine 35 on the secondary structure of the amyloid beta (Abeta(1-42)) monomer in aqueous solution, *J Phys Chem B* 112, 2159-2167, 2008; Borreguero, J. M., et al., Folding events in the 21-30 region of amyloid beta-protein (Abeta) studied in silico, *Proc Natl Acad Sci USA* 102, 6015-6020, 2005). For example, the Aβ fragment A21-A30 displayed protease resistance in limited proteolysis, indicating the formation of a stable structure within this sequence[6] (Lazo, N. D., et al., On the nucleation of amyloid beta-protein monomer folding, *Protein Sci* 14, 1581-1596, 2005). Five of seven familial Alzheimer's disease-linked mutations in Aβ known to render greater aggregation and toxic effects cluster within the part of this region, particularly residues E22-D23 (Levy, E., et al., Mutation of the Alzheimer's disease amyloid gene in hereditary cerebral hemorrhage, Dutch type, *Science* 248, 1124-1126, 1990; Hendriks, L., et al., Presenile dementia and cerebral haemorrhage linked to a mutation at codon 692 of the beta-amyloid precursor protein gene, *Nat Genet* 1, 218-221, 1992; Kamino, K., et al., Linkage and mutational analysis of familial Alzheimer disease kindreds for the APP gene region, *Am J Hum Genet* 51, 998-1014, 1992; Nilsberth, C., et al., The 'Arctic' APP mutation (E693G) causes Alzheimer's disease by enhanced Abeta protofibril formation, *Nat Neurosci* 4, 887-893, 2001; Grabowski, T. J., et al., Novel amyloid precursor protein mutation in an Iowa family with dementia and severe cerebral amyloid angiopathy. *Ann Neurol* 49, 697-705, 2001). These mutations were found to reduce the stability of the structure formed by residues A21-A30 and, thereby, possibly promoted structural arrangements to form high order assemblies (Grant, M. A., et al., Familial Alzheimer's disease mutations alter the stability of the amyloid beta-protein monomer folding nucleus, *Proc Natl Acad Sci USA* 104, 16522-16527, 2007). The presence of a lactam bridge between the side chains of D23 and K28 of Aβ accelerated oligomer and fibril formation (Sciarretta, K. L., et al., Abeta40-Lactam(D23/K28) models a conformation highly favorable for nucleation of amyloid, *Biochemistry* 44, 6003-6014, 2005). Unlike irregularly structured Aβ monomers in solution, monomeric Aβ bound to affibodies displayed a β hairpin conformation which is largely similar to the β strand-loop-β strand structure found in fibrils (Hoyer, W., et al., Stabilization of a beta-hairpin in monomeric Alzheimer's amyloid-beta peptide inhibits amyloid formation, *Proc Natl Acad Sci USA* 105, 5099-5104, 2008; Petkova, A. T., et al., A structural model for Alzheimer's beta-amyloid fibrils based on experimental constraints from solid state NMR, *Proc Natl Acad Sci USA* 99, 16742-16747, 2002; Luhrs, T., et al., 3D structure of Alzheimer's amyloid-beta(1-42) fibrils, *Proc Natl Acad Sci USA* 102, 17342-17347, 2005). The structure of Aβ monomeric β hairpin (=β strand-turn-β strand), however, differed from that of fibrils in terms of relative orientation of β strands and relevant hydrogen bonding pattern (Hoyer, W., et al., Stabilization of a beta-hairpin in monomeric Alzheimer's amyloid-beta peptide inhibits amyloid formation, *Proc Natl Acad Sci USA* 105, 5099-5104, 2008; Petkova, A. T., et al., A structural model for Alzheimer's beta-amyloid fibrils based on experimental constraints from solid state NMR, *Proc Natl Acad Sci USA* 99, 16742-16747, 2002). The structural changes, in particular the arrangement of β strands around the linker region, have been hypothesized to occur during formation of oligomers and their further association into fibrils (Hoyer, W., et al., Stabilization of a beta-hairpin in monomeric Alzheimer's amyloid-beta peptide inhibits amyloid formation, *Proc Natl Acad Sci USA* 105, 5099-5104, 2008). Varying the linker sequence and conformation may cause distinct twisting and bending of neighboring β strands, which may be propagated through β strands running to fibril axes resulting in morphological differences (Fandrich, M., et al., The behaviour of polyamino acids reveals an inverse side chain effect in amyloid structure formation, *EMBO J* 21, 5682-5690, 2002; Bieschke, J., et al., Alzheimer's Abeta peptides containing an isostructural backbone mutation afford distinct aggregate morphologies but analogous cytotoxicity, Evidence for a common low-abundance toxic structure(s)? *Biochemistry* 47, 50-59, 2008; Sciarretta, K. L., et al., Spatial separation of beta-sheet domains of beta-amyloid: disruption of each beta-sheet by N-methyl amino acids, *Biochemistry* 45, 9485-9495, 2006; Makabe, K., et al., Atomic structures of peptide self-assembly mimics, *Proc Natl Acad Sci USA* 103, 17753-17758, 2006).

Low molecular weight Aβ species, such as monomers and dimers, are not toxic (Haass, C., et al., Soluble protein oligomers in neurodegeneration: lessons from the Alzheimer's amyloid beta-peptide, *Nat Rev Mol Cell Biol* 8, 101-112, 2007; Kayed, R., et al., Common structure of soluble amyloid oligomers implies common mechanism of pathogenesis, *Science* 300, 486-489, 2003; Kayed, R., et al., Permeabilization of lipid bilayers is a common conformation-dependent activity of soluble amyloid oligomers in protein misfolding diseases, *J Biol Chem* 279, 46363-46366, 2004; Klyubin, I., et al., Amyloid beta protein immunotherapy neutralizes Abeta oligomers that disrupt synaptic plasticity in vivo, *Nat Med* 11, 556-561, 2005). Although the cause of neurodegeneration in AD is not fully understood, recent studies have suggested that toxicity should result from the generation of soluble intermediate aggregate species rather than from the formation of fibrillar species (Id., Glabe, C. G., Common mechanisms of amyloid oligomer pathogenesis in degenerative disease, *Neurobiol Aging* 27, 570-575, 2006). However, Aβ fibrils could serve as a potential pool of toxic species through dissociation or dynamic exchanges with other aggregates (Haass, C., et al., Soluble protein oligomers in neurodegeneration: lessons from the Alzheimer's amyloid beta-peptide, *Nat Rev Mol Cell Biol* 8, 101-112, 2007; O'Nuallain, B., et al., Thermodynamics of A beta(1-40) amyloid fibril elongation, *Biochemistry* 44, 12709-12718, 2005; Martins, I. C., et al., Lipids revert inert Abeta amyloid fibrils to neurotoxic protofibrils that affect learning in mice, *EMBO J* 27, 224-233, 2008). The detailed description of how these toxic species lead to generation of AD symptoms can be found elsewhere (Haass, C., et al., Soluble protein oligomers in neurodegeneration: lessons from the Alzheimer's amyloid beta-peptide, *Nat Rev Mol Cell Biol* 8, 101-112, 2007; Lansbury, P. T., et al., A century-old debate on protein aggregation and neurodegeneration enters the clinic, *Nature* 443, 774-779, 2006). These toxic oligomers are kinetic intermediates, and can display changes in conformation and toxic effects by subtle environmental changes (Teplow, D. B., et al., Elucidating amyloid beta-protein folding and assembly: A multidisciplinary approach, *Acc Chem Res* 39, 635-645, 2006; Wetzel, R., et al., Plasticity of amyloid fibrils, *Biochemistry* 46, 1-10, 2007; Haass, C., et al., Soluble protein oligomers in neurodegeneration: lessons from the Alzheimer's amyloid beta-peptide, *Nat Rev Mol Cell Biol* 8, 101-112, 2007; Kayed, R., et al., Common structure of soluble amyloid oligomers implies common mechanism of pathogenesis, *Science* 300, 486-489, 2003).

The present invention is a peptide probe that generates different levels of fluorescence signals upon recognition of distinct AR assemblies through its conformational change (FIG. 1B). Peptide probes contain the N-terminus, HCD and the C-terminus of Aβ, and the 'signal domain', which replaces the linker region of Aβ. The signal domain is responsible for conformation-dependent fluorescence of a nontoxic, membrane-permeable biarsenical dye, FlAsH (Adams, S. R., et al., New biarsenical ligands and tetracysteine motifs for protein labeling in vitro and in vivo: synthesis and biological applications, *J Am Chem Soc* 124, 6063-6076, 2002). A peptide probe displayed an increase in FlAsH fluorescence intensity when mixed with Aβ oligomers, but not monomers/dimers and fibrils. Unlike antibody-based methods, detection of Aβ oligomers using a peptide probe could occur rapidly without introducing significant perturbation of Aβ samples by virtue of the functional linkage between recognition and generation of signals. This functional coupling may further enable rapid identification of a peptide probe specific for certain forms of Aβ, small or large, under a well-defined solution condition from a diverse library. Taken together, the peptide probe of the present invention holds a promise in rapid and specific detection of Aβ oligomers.

Materials and Methods

Materials

PG46, an illustrative peptide probe of the present invention, was synthesized through solid-phase chemistry, purified by reverse-phase HPLC, lyophilized and confirmed by MALDI-TOF mass spectrometry by GenScript (Piscataway, N.J., USA). Lyophilized Aβ40 and Aβ42 were purchased from Anaspec (San Jose, Calif., USA) or W. M. Keck Foundation Biotechnology Resource Laboratory at Yale University (New Haven, Conn., USA). An antibody recognizing the N-terminus (D1-K16), 6E10, was purchased from Covance (Princeton, N.J., USA). An oligomer-specific polyclonal antibody, A11, was purchased from Invitrogen (Carlsbad, Calif., USA). A precision column pre-packed with Superdex 75 was purchased from GE Healthcare (Buckinghamshire, England, UK). All other chemicals were purchased from Sigma-Aldrich (St. Louis, Mo., USA) unless otherwise stated.

Other peptides can be developed for use as peptide probes. Another illustrative peptide developed for the present invention that may prove suitable as a peptide probe is PG38. PG38 and other suitable peptides can be prepared and utilized in a manner similar to that disclosed below in connection with PG46.

PG46 Sample Preparation

For initial dissolution of PG46, the lyophilized PG46 was solubilized with hexafluoroisopropanol (HFIP) at 1 mg peptide/2 ml HFIP for 3 hr. The PG46 in HFIP was then aliquoted into 20 vials (0.05 mg peptide each). The aliquoted PG46 in HFIP was lyophilized overnight. The lyophilized PG46 was stored at −80° C. until use. PG46 solutions were freshly prepared every time by solubilization of the HFIP-treated, re-lyophilized PG46 with dimethyl sulfoxide (DMSO) containing 10 mM 2-mercaptoethanol at 5 mg peptide/1 ml DMSO (≈1 mM PG46) for 1 hr. PG46 in DMSO was subsequently diluted by 100-fold into aqueous buffers containing Aβ (see "Aβ Sample preparation" below), unless otherwise mentioned. A similar dilution was made into the same buffers without Aβ as a control. The final concentration of PG46 and 2-mercaptoethanol was 0.05 mg/ml (≈10 μM) and 100 μM, respectively, unless otherwise stated.

Aβ Sample Preparation.

Aβ samples were prepared according to the established protocols where lyophilized Aβ was solubilized with DMSO (referred to as "DMSO protocol"), HFIP (referred to as "HFIP protocol") and 8M urea/pH 10 (referred to as "urea protocol") prior to dilution into phosphate buffers containing NaCl (Kayed, R., et al., Common structure of soluble amyloid oligomers implies common mechanism of pathogenesis, *Science* 300, 486-489, 2003; Kayed, R., et al., Permeabilization of lipid bilayers is a common conformation-dependent activity of soluble amyloid oligomers in protein misfolding diseases. *J Biol Chem* 279, 46363-46366, 2004; Kayed, R., et al., Fibril specific, conformation dependent antibodies recognize a generic epitope common to amyloid fibrils and fibrillar oligomers that is absent in prefibrillar oligomers, *Mol Neurodegener* 2, 18, 2007; Stine, W. B., Jr., et al., In vitro characterization of conditions for amyloid-beta peptide oligomerization and fibrillogenesis, *J Biol Chem* 278, 11612-11622, 2003; Dahlgren, K. N., et al., Oligomeric and fibrillar species of amyloid-beta peptides differentially affect neuronal viability, *J Biol Chem* 277, 32046-32053, 2002; Kayed, R., et al., Annular protofibrils are a structurally and functionally distinct type of amyloid oligomer, *J Biol Chem* 284, 4230-4237, 2009; Kim, J. R., et al., Urea modulation of beta-amyloid fibril growth: experimental studies and kinetic models, *Protein Sci* 13, 2888-2898, 2004; Kim, J. R., et al., Mechanism of accelerated assembly of beta-amyloid filaments into fibrils by KLVFFK(6), *Biophys J* 86, 3194-3203, 2004). In the DMSO protocol, lyophilized Aβ40 was first dissolved in HFIP at ~4 mg peptide/1 ml HFIP for overnight at a room temperature. Aβ in HFIP was then lyophilized again and stored at −80° C. until use. The HFIP-treated, re-lyophilized Aβ was resolubilized with 50 μl of DMSO per mg of peptide for 20 min, followed by direct dilution into pre-filtered phosphate-buffered saline with azide ((PBSA) 0.01 M $Na_2HPO_4/NaH_2PO_4$, 0.15 M NaCl, 0.02% (w/v) $NaN_3$, pH 7.4). In the HFIP protocol, 2.5 mg/ml of Aβ in HFIP was 10-fold diluted into PBSA and the HFIP was evaporated by applying a gentle stream of $N_2$ for at least 3 hrs. In the urea protocol, 8M urea was first prepared in 10 mM glycine-NaOH buffer, pH 10, then filtered through 0.22 μm filters. Lyophilized Aβ was then solubilized at a concentration of 10-12 mg/ml using prefiltered 8M urea, pH 10 for 30 min. Samples were then diluted into filtered PBSA. In all cases, PBSA was filtered through 0.22-μm filters and samples prepared in glass vials.

Figure 4:
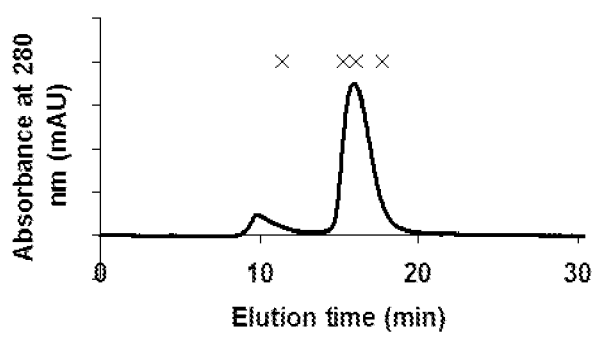
FIG. 4 is a representative size exclusion chromatography (SEC) elution profile of Aβ40 at 0.6 mg/ml in the aqueous buffer. Mobile phase was the same aqueous buffer. The mobile phase flow rate was 0.1 ml/min and elution peaks were detected by UV absorbance at 280 nm. Molecular mass of Aβ40 peak was determined by calibration of column using insulin chain B (3.5 kDa), ubiquitin (8.5 kDa), ribonuclease A (13.7 kDa) and bovine serum albumin (67 kDa). The X marks above the SEC spectrum represent elution times of bovine serum albumin, ribonuclease A, ubiquitin and insulin chain B from the left to the right, respectively. The fraction of Aβ40 solution eluting at 16 min (corresponding to the largest peak) was collected and named "Aβ40 monomer/dimer" samples. "Aβ42 monomer/dimer" samples were prepared similarly.

Aβ40 and Aβ42 monomers/dimers samples were obtained by injection of Aβ in aqueous buffers, freshly prepared according to the DMSO and urea protocols, to the size exclusion chromatography (SEC) column (superdex75) on a GE fast protein liquid chromatography (FPLC) system followed by fractionation (FIG. 4). Aβ40 oligomer samples were obtained by incubation of 1 mg/ml Aβ40 in aqueous buffers, prepared according to the DMSO protocol, at 37° C. for 3 days without stirring. No significant precipitation occurred after this incubation (data not shown). The samples contained 5% DMSO (v/v). Samples of oligomeric Aβ40 Dutch and Aβ40 Artic mutants were similarly obtained by incubation of Aβ40 Dutch and Aβ40 Artic in aqueous buffers, prepared according to the DMSO protocol, at 37° C. without stirring for 2 days and 2-3 hours, respectively. Aβ40 oligomer samples were alternatively prepared by the urea protocol. In this case, 0.25 mg/ml of Aβ40 in PBSA containing 0.4M urea was incubated at 37° C. with constant shaking at 250 rpm in a New Brunswick Scientific Innova TM4230 incubator (Edison, N.J., USA). After 24 hrs, Aβ40 solutions were centrifuged to remove precipitates and supernatants were immediately used for characterization. For Aβ42 oligomer samples, 0.5 mg/ml of Aβ42 in aqueous buffers was prepared according to the DMSO protocol, then incubated at 4° C. for 24 hrs without stirring followed by centrifugation to remove precipitates as described previously (Dahlgren, K. N., et al., Oligomeric and fibrillar species of amyloid-beta peptides differentially affect neuronal viability, *J Biol Chem* 277, 32046-32053, 2002). Aβ40 and Aβ42 fibril samples were obtained following the protocol described previously (Kayed, R., et al., Common structure of soluble amyloid oligomers implies common mechanism of pathogenesis, *Science* 300, 486-489, 2003; Kayed, R., et al., Permeabilization of lipid bilayers is a common conformation-dependent activity of soluble amyloid oligomers in protein misfolding diseases, J Biol Chem 279, 46363-46366, 2004; Kayed, R., et al., Fibril specific, conformation dependent antibodies recognize a generic epitope common to amyloid fibrils and fibrillar oligomers that is absent in prefibrillar oligomers, *Mol Neurodegener* 2, 18, 2007; Kayed, R., et al., Annular protofibrils are a structurally and functionally distinct type of amyloid oligomer, *J Biol Chem* 284, 4230-4237, 2009). Briefly, Aβ in PBSA prepared according to the HFIP protocol was incubated for 2-4 weeks at a room temperature with continuous stirring by a magnetic stir bar at 300 rpm. Samples were centrifuged to discard soluble fractions and insoluble pellets washed at least five times and resuspended with PBSA. The mass concentrations of soluble Aβ in all samples were determined by ultraviolet (UV) absorbance at 280 nm or the Bradford assay (Bradford, M. M., A rapid and sensitive method for the quantitation of microgram quantities of protein utilizing the principle of protein-dye binding, *Anal Biochem* 72, 248-254, 1976).

Size Exclusion Chromatography (SEC).

Samples were analyzed and fractionated with SEC using a precision column prepacked with Superdex 75 (GE healthcare, Buckinghamshire, England, UK) on a GE FPLC system, as described previously (Kim, J. R., et al., Urea modulation of beta-amyloid fibril growth: experimental studies and kinetic models, *Protein Sci* 13, 2888-2898, 2004; Kim, J. R., et al., Mechanism of accelerated assembly of beta-amyloid filaments into fibrils by KLVFFK(6), *Biophys J* 86, 3194-3203, 2004). Briefly, the mobile phase flow rate was set at 0.1 ml/min and elution peaks were detected by UV absorbance at 280 nm. Mobile phase buffer was matched to buffer used for preparation of Aβ samples. The column was calibrated using the following proteins as molecular weight standards: insulin chain B (3500), ubiquitin (8500), ribonuclease A (13,700), and bovine serum albumin (67,000). To determine the distribution between smaller species that could be resolved on the column (molecular mass 3-70 kDa), and larger species that could not be resolved, samples were injected without the column in place; the percent of non-aggregates (monomers+ dimers (M+D)) was calculated by dividing the M+D peak area by the peak area without the column in place.

Circular Dichroism Spectroscopy

Secondary structure of AR in solutions was determined using circular dichroism (CD), collected using an Aviv 62A DS circular spectrometer (Lakewood, N.J., USA) in the far-UV range with 0.1 cm of path length of cuvette. Ellipticity of sample containing Aβ at each wavelength was measured without dilution. The spectrum of the background was measured and then subtracted from the sample spectrum.

Dot Blot

One μg of Aβ were applied to a nitrocellulose membrane, allowed to dry at room temperatures. Membrane blocking, washing, incubation with primary and secondary antibody, development with chemiluminescence was performed according to the manufacture's protocol.

FlAsH Fluorescence Measurements.

Freshly prepared PG46 in DMSO at 5 mg/ml with 10 mM 2-mercaptoethanol was directly diluted by 100-fold into Aβ solutions or buffers without Aβ prior to addition of FlAsH. Note that neither volume nor concentration of Aβ in solution was nearly changed by the addition of 100× PG46. As another control, DMSO containing 10 mM 2-mercaptoethanol was 100-fold diluted into Aβ solutions. As a result, all samples (PG46 only, Aβ only, a mixture of PG46+Aβ contained an equal amount of DMSO and 2-mercaptoethanol, respectively. These samples were incubated for 1 hr at a room temperature. Then, 200 μM of FlAsH-(1,2-ethanedithiol (EDT))$_2$ in DMSO was 125-fold diluted into samples of PG46 only, Aβ only and a mixture of PG46+Aβ. The samples were then further incubated for an additional 1 hr prior to FlAsH fluorescence measurements using a Photon Technology Quanta-Master QM-4 spectrofluorometer (Birmingham, N.J., USA). Excitation wavelength was 508 nm and emission was monitored at 520-550 nm.

Results

Design of a peptide probe prototype. The desired property of peptide probes is the ability to modulate fluorescence signals through association with AR species, in particular oligomers (FIG. 1B). Peptide probes contain the N-terminus (D1-K16), HCD (L17-A21) and the C-terminus (I31-V40) of Aβ3, and the 'signal domain' (FIG. 1A). The Aβ N-terminus is included as its presence may reduce the self-assembly of peptide probes (Pike, C. J., et al., Amino-terminal deletions enhance aggregation of beta-amyloid peptides in vitro, *J Biol Chem* 270, 23895-23898, 1995). The HCD and C-terminal domains of Aβ undergo conformational changes during Aβ self-assembly (Teplow, D. B., et al., Elucidating amyloid beta-protein folding and assembly: A multidisciplinary approach, *Acc Chem Res* 39, 635-645, 2006; Lazo, N. D., et al., On the nucleation of amyloid beta-protein monomer folding, *Protein Sci* 14, 1581-1596, 2005; Tjernberg, L. O., et al., Arrest of beta-amyloid fibril formation by a pentapeptide ligand, *J Biol Chem* 271, 8545-8548, 1996; Soto, C., et al., Beta-sheet breaker peptides inhibit fibrillogenesis in a rat brain model of amyloidosis: implications for Alzheimer's therapy, *Nat Med* 4, 822-826, 1998; Liu, R., et al., Residues 17-20 and 30-35 of beta-amyloid play critical roles in aggregation, *J Neurosci Res* 75, 162-171, 2004; Christopeit, T., et al., Mutagenic analysis of the nucleation propensity of oxidized Alzheimer's beta-amyloid peptide, *Protein Sci* 14, 2125-2131, 2005; Chimon, S., et al., Evidence of fibril-like beta-sheet structures in a neurotoxic amyloid intermediate of Alzheimer's beta-amyloid, *Nat Struct Mol Biol,* 2007; Losic, D., et al., High resolution scanning tunnelling microscopy of the beta-amyloid protein (Abeta1-40) of Alzheimer's disease suggests a novel mechanism of oligomer assembly, *J Struct Biol* 155, 104-110, 2006; Mastrangelo, I. A., et al., High-resolution atomic force microscopy of soluble Abeta42 oligomers, *J Mol Biol* 358, 106-119, 2006; Petkova, A. T., et al., A structural model for Alzheimer's beta-amyloid fibrils based on experimental constraints from solid state NMR, *Proc Natl Acad Sci USA* 99, 16742-16747, 2002; Luhrs, T., et al., 3D structure of Alzheimer's amyloid-beta(1-42) fibrils, *Proc Natl Acad Sci USA* 102, 17342-17347, 2005). These conformational changes are utilized in a peptide probe for its functional coupling between binding to Aβ and fluorescence signaling. The HCD and C-terminal domains will also provide a peptide probe with binding affinity toward Aβ, as they are critical in Aβ self-assembly (Tjernberg, L. O., et al., Arrest of beta-amyloid fibril formation by a pentapeptide ligand, *J Biol Chem* 271, 8545-8548, 1996; Soto, C., et al., Beta-sheet breaker peptides inhibit fibrillogenesis in a rat brain model of amyloidosis: implications for Alzheimer's therapy, *Nat Med* 4, 822-826, 1998; Liu, R., et al., Residues 17-20 and 30-35 of beta-amyloid play critical roles in aggregation, *J Neurosci Res* 75, 162-171, 2004; Christopeit, T., et al., Mutagenic analysis of the nucleation propensity of oxidized Alzheimer's beta-amyloid peptide, *Protein Sci* 14, 2125-2131, 2005). The signal domain is responsible for conformation-dependent fluorescence generation. A tetracystein motif such as CCXXCC (X: a noncystein amino acid) is included in the signal domain (FIG. 1A-B). The signal domain forms the conditional binding site of a nontoxic, membrane-permeable biarsenical fluorescent dye, FlAsH (Adams, S. R., et al., New biarsenical ligands and tetracysteine motifs for protein labeling in vitro and in vivo: synthesis and biological applications, *J Am Chem Soc* 124, 6063-6076, 2002). FlAsH becomes fluorescent (>50,000×) very rapidly, within a few seconds to minutes, upon binding to the tetracystein motif (Id.). The structures of adjacent flanking sequences would affect the conformation of the tetracystein motif and, therefore, differentiate FlAsH binding and fluorescence (Id.; Ignatova, Z., et al., Monitoring protein stability and aggregation in vivo by real-time fluorescent labeling, *Proc Natl Acad Sci USA* 101, 523-528, 2004; Madani, F., et al., Hairpin structure of a biarsenical-tetracysteine motif determined by NMR spectroscopy, *J Am Chem Soc* 131, 4613-4615, 2009; Martin, B. R., et al., Mammalian cell-based optimization of the biarsenical-binding tetracysteine motif for improved fluorescence and affinity, *Nat Biotechnol* 23, 1308-1314, 2005). Based on these findings, we reasoned that functional coupling between Aβ recognition and fluorescence signaling could be achieved by the conformational change of a peptide probe, particularly in the signal domain and the neighboring HCD and C-terminal domains, upon binding to A. Structural arrangements of HCD, the C-terminus and the linker region of Aβ are different in monomers, oligomers and fibrils (Teplow, D. B., et al., Elucidating amyloid beta-protein folding and assembly: A multidisciplinary approach, *Acc Chem Res* 39, 635-645, 2006; Fernandez-Busquets, X., et al., Recent structural and computational insights into conformational diseases, *Curr Med Chem* 15, 1336-1349, 2008; Lazo, N. D., et al., On the nucleation of amyloid beta-protein monomer folding, *Protein Sci* 14, 1581-1596, 2005; Wetzel, R., et al., Plasticity of amyloid fibrils, *Biochemistry* 46, 1-10, 2007; Zhang, S., et al., The Alzheimer's peptide a beta adopts a collapsed coil structure in water, *J Struct Biol* 130, 130-141, 2000; Lee, J. P., et al., 1H NMR of A beta amyloid peptide congeners in water solution. Conformational changes correlate with plaque competence, *Biochemistry* 34, 5191-5200, 1995; Riek, R., et al., NMR studies in aqueous solution fail to identify significant conformational differences between the monomeric forms of two Alzheimer peptides with widely different plaque-competence, A beta(1-40)(ox) and A beta(1-42)(ox), *Eur J Biochem* 268, 5930-5936, 2001; Hou, L., et al., Solution NMR studies of the A beta(1-40) and A beta(1-42) peptides establish that the Met35 oxidation state affects the mechanism of amyloid formation, *J Am Chem Soc* 126, 1992-2005, 2004; Lansbury, P. T., Jr., Evolution of amyloid: what normal protein folding may tell us about fibrillogenesis and disease, *Proc Natl Acad Sci USA* 96, 3342-3344, 1999; Walsh, D. M., et al., Amyloid beta-protein fibrillogenesis. Structure and biological activity of protofibrillar intermediates, *J Biol Chem* 274, 25945-25952, 1999; Huang, T. H., et al., Structural studies of soluble oligomers of the Alzheimer beta-amyloid peptide, *J Mol Biol* 297, 73-87, 2000; Nichols, M. R., et al., Growth of beta-amyloid(1-40) protofibrils by monomer elongation and lateral association, Characterization of distinct products by light scattering and atomic force microscopy, *Biochemistry* 41, 6115-6127, 2002; Barghorn, S., et al., Globular amyloid beta-peptide oligomer—a homogenous and stable neuropathological protein in Alzheimer's disease, *J Neurochem* 95, 834-847, 2005; Chimon, S., et al., Capturing intermediate structures of Alzheimer's beta-amyloid, Abeta(1-40), by solid-state NMR spectroscopy, *J Am Chem Soc* 127, 13472-13473, 2005; Chimon, S., et al., Evidence of fibril-like beta-sheet structures in a neurotoxic amyloid intermediate of Alzheimer's beta-amyloid, *Nat Struct Mol Biol,* 2007; Losic, D., et al., High resolution scanning tunnelling microscopy of the beta-amyloid protein (Abeta1-40) of Alzheimer's disease suggests a novel mechanism of oligomer assembly, *J Struct Biol* 155, 104-110, 2006; Mastrangelo, I. A., et al., High-resolution atomic force microscopy of soluble Abeta42 oligomers, *J Mol Biol* 358, 106-119, 2006; Hoyer, W., et al., Stabilization of a beta-hairpin in monomeric Alzheimer's amyloid-beta peptide inhibits amyloid formation, *Proc Natl Acad Sci USA* 105, 5099-5104, 2008; Habicht, G., et al., Directed selection of a conformational antibody domain that prevents mature amyloid fibril formation by stabilizing Abeta protofibrils, *Proc Natl Acad Sci USA* 104, 19232-19237, 2007; Petkova, A. T., et al., A structural model for Alzheimer's beta-amyloid fibrils based on experimental constraints from solid state NMR, *Proc Natl Acad Sci USA* 99, 16742-16747, 2002; Luhrs, T., et al., 3D structure of Alzheimer's amyloid-beta(1-42) fibrils, *Proc Natl Acad Sci USA* 102, 17342-17347, 2005; Whittemore, N. A., et al., Hydrogen-deuterium (H/D) exchange mapping of Abeta 1-40 amyloid fibril secondary structure using nuclear magnetic resonance spectroscopy, *Biochemistry* 44, 4434-4441, 2005; Williams, A. D., et al., Alanine scanning mutagenesis of Abeta(1-40) amyloid fibril stability, *J Mol Biol* 357, 1283-1294, 2006; Williams, A. D., et al., Mapping abeta amyloid fibril secondary structure using scanning proline mutagenesis, *J Mol Biol* 335, 833-842, 2002; Torok, M., et al., Structural and dynamic features of Alzheimer's Abeta peptide in amyloid fibrils studied by site-directed spin labeling, *J Biol Chem* 277, 40810-40815, 2002; Grant, M. A., et al., Familial Alzheimer's disease mutations alter the stability of the amyloid beta-protein monomer folding nucleus, *Proc Natl Acad Sci USA* 104, 16522-16527, 2007; Baumketner, A., et al., Amyloid beta-protein monomer structure: a computational and experimental study, *Protein Sci* 15, 420-428, 2006; Baumketner, A., et al., The structure of the Alzheimer amyloid beta 10-35 peptide probed through replica-exchange molecular dynamics simulations in explicit solvent, *J Mol Biol* 366, 275-285, 2007; Triguero, L., et al., Molecular dynamics study to investigate the effect of chemical substitutions of methionine 35 on the secondary structure of the amyloid beta (Abeta(1-42)) monomer in aqueous solution, *J Phys Chem B* 112, 2159-2167, 2008; Borreguero, J. M., et al., Folding events in the 21-30 region of amyloid beta-protein (Abeta) studied in silico, *Proc Natl Acad Sci USA* 102, 6015-6020, 2005). For these reasons, it was hypothesized that the binding of a peptide probe to distinct Aβ species would produce different levels of FlAsH fluorescence. The initial peptide probe, PG46 (FIG. 1A), contains CCPGCC, the most effective tetracystein sequence for FlAsH fluorescence (Adams, S. R., et al., New biarsenical ligands and tetracysteine motifs for protein labeling in vitro and in vivo: synthesis and biological applications, *J Am Chem Soc* 124, 6063-6076, 2002; Martin, B. R., et al., Mammalian cell-based optimization of the biarsenical-binding tetracysteine motif for improved fluorescence and affinity, *Nat Biotechnol* 23, 1308-1314, 2005). Additional residues (HRW and KTF) were introduced on both ends of the tetracystein motif in PG46 to improve FlAsH binding and fluorescence (Martin, B. R., et al., Mammalian cell-based optimization of the biarsenical-binding tetracysteine motif for improved fluorescence and affinity, *Nat Biotechnol* 23, 1308-1314, 2005).

Preparation and Characterization of PG46 Solution

Figure 5:
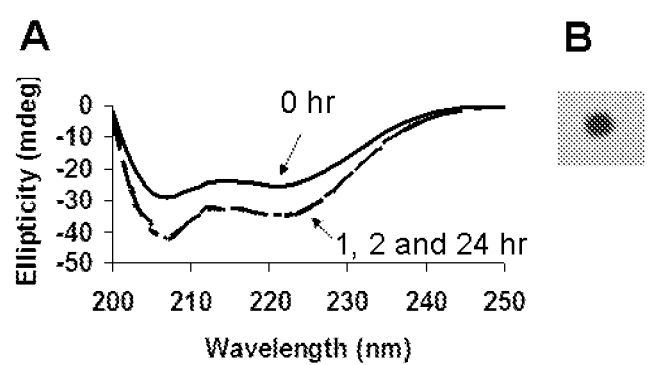
FIG. 5A is a circular dichroism (CD) spectra of 0.5 mg/ml PG46 during incubation in HFIP at RT. CD signals were changed over time during the first several minute of incubation of PG46 in HFIP, then remained same after 1 hr, implying neither further occurrence of dissolution nor α-helical formation of PG46.
FIG. 5B is a dot blot assay of PG46 using an oligomer-specific polyclonal antibody, A11.
Figure 6:
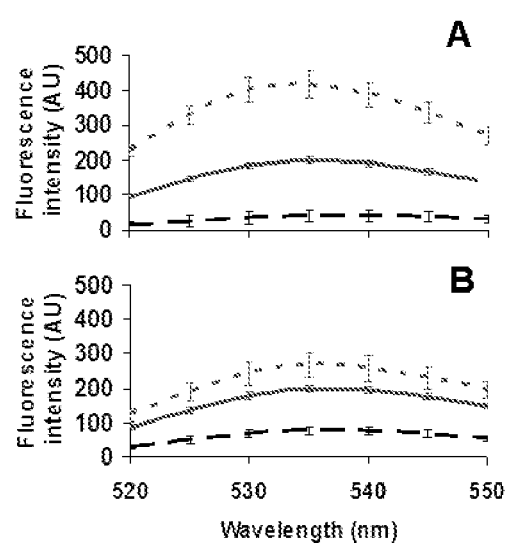
FIG. 6A is a FlAsH fluorescence of PG46 when mixed with Aβ40 Dutch oligomer samples. Fluorescence spectra of samples containing Aβ only, PG46 only, and Aβ+PG46 are represented by black long dash lines, green solid lines and red dot lines, respectively. For FlAsH measurements, samples of Aβ only, PG46 only and Aβ+PG46 were incubated at 25° C. without agitation for 1 hr prior to addition of FlAsH followed by additional 1 hr incubation. The excitation wavelength was 508 nm. The mass concentration of PG46 was 0.05 mg/ml. n≤3. The error bar represents one standard deviation.
FIG. 6B is a FlAsH fluorescence of PG46 when mixed with Aβ40 Artic oligomer samples. Fluorescence spectra of samples containing Aβ only, PG46 only, and Aβ+PG46 are represented by black long dash lines, green solid lines and red dot lines, respectively. For FlAsH measurements, samples of Aβ only, PG46 only and Aβ+PG46 were incubated at 25° C. without agitation for 1 hr prior to addition of FlAsH followed by additional 1 hr incubation. The excitation wavelength was 508 nm. The mass concentration of PG46 was 0.05 mg/ml. n≤3. The error bar represents one standard deviation.

PG46 contains HCD and the C-terminus of Aβ, and therefore is prone to aggregation. Since FlAsH fluorescence of PG46 may depend on structures of the signal domain and its flanking sequences, which could also be influenced by aggregation states, a well-characterized and reproducible initial condition was needed to minimize variation from run to run. To this end, the lyophilized PG46 was first solubilized at 0.5 mg/ml with HFIP, known to promote formation of a helical structures of many amyloidogenic peptides including Aβ (Teplow, D. B., Preparation of amyloid beta-protein for structural and functional studies, *Methods Enzymol* 413, 20-33, 2006). As expected, PG46 also displayed a predominant a helical structure as determined by CD (supporting FIG. 5A). CD signals were changed over time during the first few minute of incubation of PG46 in HFIP, then remained unchanged after then (supporting FIG. 5A), implying no further occurrence of dissolution or a helical formation of PG46. Based on this finding, PG46 was incubated in HFIP for 3 hrs and then lyophilized for all the experiments.

The fresh PG46 solution was prepared by redissolution of the HFIP-treated, lyophilized PG46 with DMSO containing 10 mM 2-mercaptoethanl at 5 mg/ml. Then, PG46 solutions were rapidly diluted into PBSA. First, the aggregation state of freshly prepared PG46 in aqueous buffers using SEC was determined. To determine the fraction of PG46 in aggregated versus non-aggregated (monomers/dimers) form, peak areas were compared for identical samples injected with and without the SEC column in place as described previously and results were summarized in Table 1 (Kim, J. R., et al., Urea modulation of beta-amyloid fibril growth: experimental studies and kinetic models, *Protein Sci* 13, 2888-2898, 2004; Kim, J. R., et al., Mechanism of accelerated assembly of beta-amyloid filaments into fibrils by KLVFFK(6), *Biophys J* 86, 3194-3203, 2004). The freshly prepared PG46 was mostly monomeric at ≤0.002 mg/ml (=0.4 μM). In contrast, oligomerization of PG46 occurred immediately after dilution into PBSA at ≤0.01 mg/ml (=2 μM). Oligomeric PG46 was found to be dominantly present at 0.05 mg/ml (Table 1). Filtration of PG46 solution at 0.05 mg/ml with a 50 kDa cut-off membrane was carried out and provided similar results. Nearly all of PG46 in aqueous buffers at 0.05 mg/ml existed as oligomers of >50 kDa in size. No visible precipitate was observed from PG46 solutions for at least 4 hrs. Taken together, the results indicate that the predominant fraction of PG46 at 0.05 mg/ml was soluble oligomers. PG46 oligomers were SDS-labile; it was dissociated into monomers in a SDS-PAGE (data not shown). PG46 oligomers were recognizable by A11 (supporting FIG. 5B), a polyclonal antibody capable of detecting a common backbone structures found in oligomers formed by amyloidogenic peptides/proteins with various primary sequences. PG46 at 0.05 mg/ml was used for most FlAsH fluorescence measurements described below.

FlAsH fluorescence of 0.05 mg/ml (=~10 μM) PG46 was measured with an increasing concentration of FlAsH; the fluorescence intensity leveled off at >0.5 μM FlAsH (FIG. 1C). This also indicates that the majority of PG46 molecules were not accessible to FlAsH, presumably because of oligomeric nature of PG 46. For FlAsH fluorescence measurements with Aβ, 0.05 mg/ml of PG46 and 1.6 μM of FlAsH were used.

Characterization of Aβ40 Samples—Monomers/Dimers, Oligomers and Fibrils.

Figure 2:
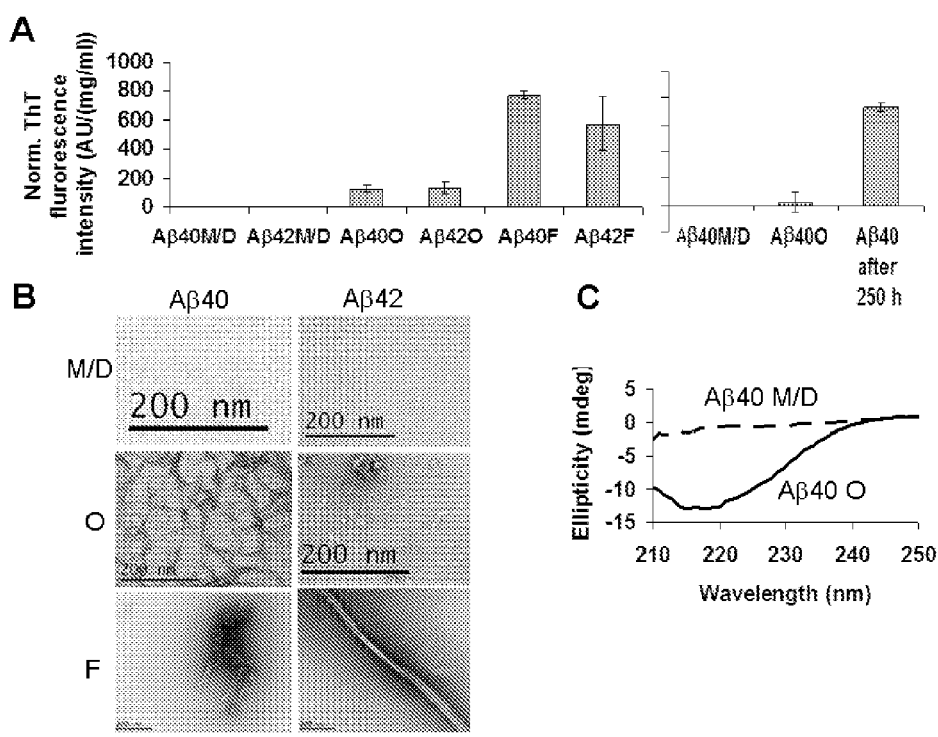
FIG. 2A is the thioflavin T fluorescence of Aβ40 monomers/dimers (Aβ40 M/D), Aβ42 monomers/dimers (Aβ42 M/D), Aβ40 oligomers (Aβ40 O), Aβ42 oligomers (Aβ42 O), Aβ40 fibrils (Aβ40 F), and Aβ42 fibrils (Aβ42 F). Samples were prepared according to (left) the DMSO or HFIP protocol and (right) the urea protocol. Thioflavin T fluorescence of Aβ at 0.25 mg/ml incubated in PBSA containing 0.4M urea after 250 hr incubation at 37° C. with constant shaking at 250 rpm was shown for comparison.
FIG. 2B are TEM images of Aβ40 M/D, Aβ42 M/D, Aβ40 O, Aβ42 O, Aβ42 F and Aβ42 F. All samples were prepared according to the DMSO or HFIP protocol. Scale bars represent 200 nm.
FIG. 2C is a circular dichroism (CD) spectra of Aβ40 O and Aβ40 M/D prepared according to the urea protocol.
Figure 3:
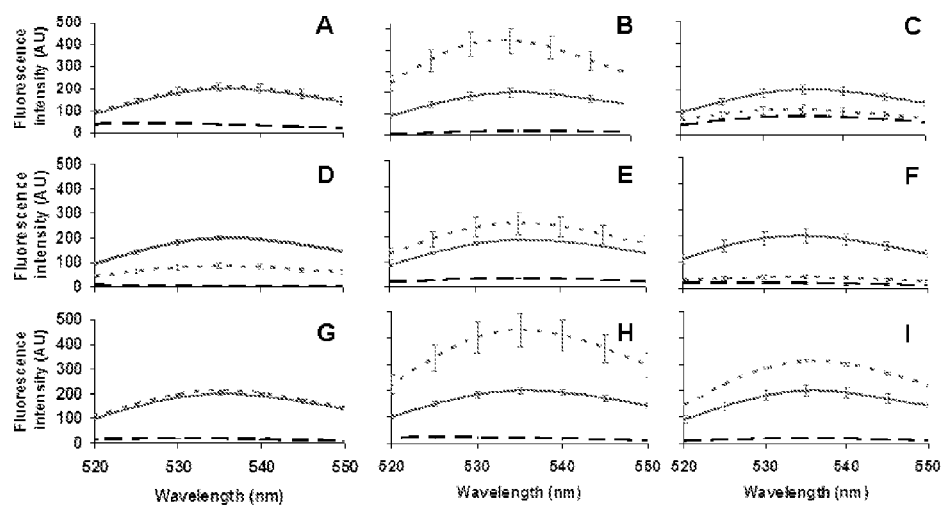
FIG. 3 are FlAsH fluorescence spectra of PG46 when mixed with samples containing (A and G) Aβ40 monomers/dimers, (B, H and I) Aβ40 oligomers, (C) Aβ40 fibrils, (D) Aβ42 monomers/dimers, (E) Aβ42 oligomers and (F) Aβ42 fibrils. Aβ samples were prepared according to (A, B, D, E and I) the DMSO, (C and F) HFIP and (G and H) urea protocols. The mass concentrations of Aβ were 0.05 mg/ml in (I) and 0.1 mg/ml in all the other samples, respectively. Fluorescence spectra of samples containing Aβ only, PG46 only, and Aβ+PG46 are represented by black long dash lines, green solid lines, and red dot lines, respectively. For FlAsH measurements, samples of Aβ only, PG46 only and Aβ+PG46 were incubated at 25° C. without agitation for 1 hr prior to addition of FlAsH followed by additional 1 hr incubation before fluorescence measurements. The excitation wavelength was 508 nm. The mass concentration of PG46 was 0.05 mg/ml. n≥3. The error bar represents one standard deviation.

"Aβ40 monomer/dimer" samples, prepared according to the DMSO and urea protocols followed by SEC fractionation, displayed no significant fluorescence when mixed with Thioflavin T (ThT) (FIG. 2A), a fluorescent dye specific for β-sheet structures found in amyloid fibrils (LeVine, H., 3rd., Quantification of beta-sheet amyloid fibril structures with thioflavin T, *Methods Enzymol* 309, 274-284, 1999). No aggregate was detected in transmission electron microscopy (TEM) of these samples (FIG. 2B). Aβ40 monomers/dimers prepared according to the urea protocol were largely irregularly structured as determined by CD (FIG. 2C). "Aβ42 monomer/dimer" samples were prepared according to the DMSO protocols. No strong ThT fluorescence was observed from these samples as in Aβ40 monomers/dimers (FIG. 2A). TEM images of Aβ42 monomer/dimer samples collected from SEC showed the presence of a dominant fraction of non-aggregated species (FIG. 2B).

"Aβ40 soluble oligomer" samples displayed a slightly increased ThT fluorescence intensity compared to Aβ40 monomer/dimer samples (FIG. 2A). ThT fluorescence signals from these samples were significantly low compared to those from fibril samples (FIG. 2A). SEC and membrane filtration analyses confirmed that a predominant fraction (~80%) of these samples, prepared according to the DMSO and urea protocols, was oligomeric (>50 kDa) with the remainder being lower molecular weight species such as monomers/dimers (data not shown). These samples appeared predominantly as worm-like curvilinear particles in a TEM image (FIG. 2B). "Aβ42 soluble oligomer" samples were prepared following the DMSO protocol and found to display low ThT fluorescence compared to fibrils (FIG. 2A). Small prefibrillar particles were detected in a TEM image of these samples (FIG. 2B). No further separation was made for both Aβ40 and Aβ42 oligomeric samples.

"Aβ40 fibril" and "Aβ42 fibril" samples were separated from soluble species by centrifugation. These samples exhibited much higher ThT fluorescence intensity compared to other Aβ samples (FIG. 2A). The presence of mature fibrils in these samples was confirmed by TEM (FIG. 2B).

FlAsH Fluorescence.

FlAsH fluorescence of PG46 at 0.05 mg/ml was measured in the presence of different Aβ species, such as monomers/dimers, soluble oligomers and fibrils. PG 46 was freshly prepared each time and coincubated with Aβ samples. Incubation with Aβ40 monomers/dimers yielded no significant change of FlAsH fluorescence of PG46 (FIG. 2A and G). In contrast, FlAsH fluorescence almost doubled when PG46 was mixed with Aβ40 soluble oligomers (FIG. 2B and H). Incubation of PG46 with Aβ40 fibrils resulted in a decrease in FlAsH fluorescence (FIG. 2C). FlAsH fluorescence responses of PG46 were similar when mixed with Aβ samples prepared according to the different protocol (e.g., DMSO vs. urea protocols) (FIGS. 2A and G, and B and H). FlAsH fluorescence intensity of PG46 appeared to increase with an increasing mass concentration of Aβ soluble oligomers from 0 to 0.1 mg/ml followed by a level-off with a further addition of Aβ (data not shown). FlAsH fluorescence intensity of PG46 was reduced when mixed with Aβ42 monomers/dimers (FIG. 2D) and Aβ42 fibrils (FIG. 2F). A slight increase in FlAsH fluorescence intensity was observed when PG46 mixed with Aβ42 oligomers. The FlAsH fluorescence signals of PG46 were low with Aβ42 oligomers compared to Aβ40 oligomers. FlAsH fluorescence of PG46 was found to increase when mixed with oligomers formed by Aβ40 Artic (E22G) and Dutch (E22Q) mutants (FIG. S3).

Amino Acid Sequences.

The following are sequences illustrative of probes developed for the present invention:

PG46:
DAEFRHDSGYEVHHQKLVFFA*EHRWCCPGCCKTFGA*IIGLMVGGVV

PG38:
DAEFRHDSGYEVHHQKLVFFA*ECCPGCCGA*IIGLMVGG

The following are sequences of illustrative beta amyloid (Aβ) probed using the present invention:

Aβ40: DAEFRHDSGYEVHHQKLVFFA*EDVGSNKGA*IIGLMVGGVV

Aβ42: DAEFRHDSGYEVHHQKLVFFA*EDVGSNKGA*IIGLMVGGVVIA

Other embodiments of the invention include a peptide probe comprising PG46, a peptide probe consisting essentially of PG46, and a peptide probe for the detection of amyloid aggregation comprising PG46. Still other embodiments of the invention include a peptide probe comprising PG38, a peptide probe consisting essentially of PG38, and a peptide probe for the detection of amyloid aggregation comprising PG38.

Another embodiment of the invention is a method for producing a peptide probe comprising the steps of:

a) lyophilizing a peptide;

b) solubilizing the lyophilized peptide of step a) with hexafluoroisopropanol (HFIP) at 1 mg peptide/2 ml HFIP for 3 hr;

c) aliquoting the peptide of step b) in HFIP into 20 vials of 0.05 mg peptide each;

d) lyophilizing the aliquoted peptide of step c) in HFIP;

e) solubilizing the lyophilized peptide of step d) with dimethyl sulfoxide (DMSO) containing 10 mM 2-mercaptoethanol at 5 mg peptide/1 ml DMSO (>>1 mM PG46) for 1 hr; and f) diluting the peptide of step e) in DMSO by 100-fold into aqueous buffers containing Aβ.

In this method, illustrative peptides include PG46 and PG38.

The foregoing detailed description of the preferred embodiments and the appended figures and references, which are incorporated herein in their entireties, have been presented only for illustrative and descriptive purposes. They are not intended to be exhaustive and are not intended to limit the scope and spirit of the invention. The embodiments were selected and described to best explain the principles of the invention and its practical applications. One skilled in the art will recognize that many variations can be made to the invention disclosed in this specification without departing from the scope and spirit of the invention.

TABLE 1

Population of Soluble Species in PG46 Samples

| | Concentration (mg/ml) | | | |
|---|---|---|---|---|
| | 0.002 | 0.01 | 0.05 | 0.05 |
| Method of determination | SEC[a] | SEC[a] | SEC[a] | Membrane filtration[b] |
| % of monomer + dimer[c] | 90 ± 35 | 20 ± 4 | <1 | NA |
| % of oligomer[d] | ~10 | 80 ± 4 | >99 | NA |
| % of species with <50 kDa | NA | NA | NA | ~1 |
| % of species with 50-100 kDa | NA | NA | NA | 20 ± 4 |
| % of species with >100 kDa | NA | NA | NA | 80 ± 4 |

[a] Population of soluble species determined by the size exclusion chromatography (SEC) using Superdex75. The data were analyzed as described previously[79-80].

[b] Population of soluble species determined by filtration with membranes with cut-off pore sizes of 50 and 100 kDa. The percentage of each fraction was calculated by measuring the absorbance at 280 nm of samples before and after filtration.

[c] Apparent MW <10 kDa as determined by SEC.

[d] Apparent MW >70 kDa as determined by SEC.

Errors represent one standard deviation (n ≥ 3)

What is claimed is:

1. A peptide probe for the rapid and specific detection of β-amyloid (Aβ) aggregation, comprising a peptide, wherein the peptide probe displays increased emitted fluorescence signals upon coincubation with Aβ oligomers, but not with Aβ monomers or Aβ dimers or Aβ fibrils, relative to the absence of Aβ, wherein the amino acid sequence of Aβ is DAEFRHDS-GYEVHHQKLVFFAEDVGSNKGAIIGLMVGGVV;

wherein the Aβ monomers are polypeptides containing 40 amino acids, wherein the Aβ dimers are non-covalent complexes of two Aβ monomers, wherein the Aβ oligomers are non-covalent complexes of more than two Aβ monomers, wherein the Aβ monomers, the Aβ dimers and the Aβ oligomers are soluble in an aqueous buffer, and wherein the Aβ fibrils are insoluble non-covalent complexes of a multiple of the Aβ monomers.

2. The peptide probe as claimed in claim 1, wherein the increased emitted fluorescence signals are displayed rapidly upon recognition by the peptide probe of the Aβ oligomers.

3. The peptide probe as claimed in claim 2, wherein the detection of β-amyloid (Aβ) aggregation occurs within two hours after addition of the peptide probe into the aqueous buffer, which contain Aβ.

4. The peptide probe as claimed in claim 3, wherein the signal domain is a binding site for a specific nontoxic, membrane-permeable biarsenical fluorescence dye, FlAsH, and to which the FlAsH is bound.

5. The peptide probe as claimed in claim 4, wherein the peptide probe generates different levels of fluorescence signals upon recognition of distinct Aβ assemblies by the peptide probe.

6. The peptide probe as claimed in claim 2, having an ability to modulate the fluorescence signals generated by the peptide probe through association with Aβ species.

7. The peptide probe as claimed in claim 6, wherein the Aβ species are Aβ oligomers, wherein the Aβ oligomers are non-covalent complexes of more than two Aβ monomers, wherein the Aβ monomers are polypeptides containing 40 amino acids, and wherein the Aβ monomers and the Aβ oligomers are soluble in aqueous buffers.

8. The peptide probe as claimed in claim 7, wherein the peptide probe is PG46 having an amino acid sequence of DAEFRHDSGYEVHHQKLVFFAEHRWC-CPGCCKTFGAIIGLMVGGVV.

9. The peptide probe as claimed in claim 2, wherein the peptide probe is PG46 having an amino acid sequence of DAEFRHDSGYEVHHQKLVFFAEHRWC-CPGCCKTFGAIIGLMVGGVV.

10. A peptide probe for the rapid and specific detection of β-amyloid (Aβ) aggregation comprising a peptide, wherein:
the amino acid sequence of Aβ is DAEFRHDSGYEVH-HQKLVFFAEDVGSNKGAIIGLMVGGVV;
the peptide probe generates fluorescence signals rapidly upon coincubation with Aβ oligomers, but not with Aβ monomers or Aβ dimers or Aβ fibrils, relative to the absence of Aβ,
wherein the Aβ monomers are polypeptides containing 40 amino acids,
wherein the Aβ dimers are non-covalent complexes of two Aβ monomers,
wherein the Aβ oligomers are non-covalent complexes of more than two Aβ monomers,
wherein the Aβ monomers, the Aβ dimers and the Aβ oligomers are soluble in an aqueous buffer, and
wherein the Aβ fibrils are insoluble non-covalent complexes of a multiple of the Aβ monomers.

11. The peptide probe as claimed in claim 10, wherein the signal domain is a binding site for a specific nontoxic, membrane-permeable biarsenical fluorescence dye, FlAsH, and to which the FlAsH is bound.

12. The peptide probe as claimed in claim 11, wherein the peptide probe generates different levels of fluorescence signals upon recognition of distinct Aβ assemblies by the peptide probe.

13. The peptide probe as claimed in claim 12, wherein the peptide probe is PG46 having an amino acid sequence of DAEFRHDSGYEVHHQKLVFFAEHRWC-CPGCCKTFGAIIGLMVGGVV.

14. A peptide probe for the rapid and specific detection of β-amyloid (Aβ) aggregation comprising a peptide that has been lyophilized, then solubilized with 1,1,1,3,3,3-hexafluoro-2-propanol, then lyophilizing again, then solubilized with dimethyl sulfoxide, and then diluted into an aqueous buffer, wherein:
the amino acid sequence of Aβ is DAEFRHDSGYEVH-HQKLVFFAEDVGSNKGAIIGLMVGGVV;
the peptide probe generates fluorescence signals rapidly upon coincubation with Aβ oligomers, but not with Aβ monomers or Aβ dimers or Aβ fibrils, relative to the absence of Aβ,
wherein the Aβ monomers are polypeptides containing 40 amino acids,
wherein the Aβ dimers are non-covalent complexes of two Aβ monomers,
wherein the Aβ oligomers are non-covalent complexes of more than two Aβ monomers,
wherein the Aβ monomers, the Aβ dimers and the Aβ oligomers are soluble in aqueous buffers, and
wherein the Aβ fibrils are insoluble non-covalent complexes of a multiple of the Aβ monomers.

15. The peptide probe as claimed in claim 14, wherein the detection of β-amyloid (Aβ) aggregation occurs within two hours after addition of the peptide probe into the aqueous buffer, which contain Aβ.

16. The peptide probe as claimed in claim 15, comprising an N-terminus of Aβ, a hydrophobic central domain of Aβ, a signal domain and a C-terminus of Aβ in an order from an N-terminal residue of the peptide probe to a C-terminal residue of the peptide probe,
wherein the amino acid sequence of the N-terminus of Aβ is DAEFRHDSGYEVHHQK,
wherein the amino acid sequence of the hydrophobic central domain of Aβ is LVFFA,
wherein the amino acid sequence of the signal domain is EHRWCCPGCCKTFGA, and
wherein the amino acid sequence of the C-terminus of Aβ is IIGLMVGGVV.

17. The peptide probe as claimed in claim 16, wherein the signal domain is a binding site for a specific nontoxic, membrane-permeable biarsenical fluorescence dye, FlAsH, and to which the FlAsH is bound.

18. The peptide probe as claimed in claim 17, wherein the peptide probe generates different levels of fluorescence signals upon recognition of distinct Aβ assemblies by the peptide probe.

19. The peptide probe as claimed in claim 14, having an ability to modulate the fluorescence signals generated by the peptide probe through association with Aβ species.

20. The peptide probe as claimed in claim 19, wherein the Aβ species are Aβ oligomers,
wherein the Aβ oligomers are non-covalent complexes of more than two Aβ monomers,
wherein the Aβ monomers are polypeptides containing 40 amino acids, and
wherein the Aβ monomers and the Aβ oligomers are soluble in aqueous buffers.

21. The peptide probe as claimed in claim 20, comprising an N-terminus of Aβ, a hydrophobic central domain of Aβ, a signal domain and a C-terminus of Aβ, in an order from an N-terminal residue of the peptide probe to a C-terminal residue of the peptide probe,
wherein the amino acid sequence of the N-terminus of Aβ is DAEFRHDSGYEVHHQK,
wherein the amino acid sequence of the hydrophobic central domain of Aβ is LVFFA,
wherein the amino acid sequence of the signal domain is EHRWCCPGCCKTFGA, and
wherein the amino acid sequence of the C-terminus of Aβ is IIGLMVGGVV.

22. The peptide probe as claimed in claim 14, wherein the peptide probe is PG46 having the amino acid sequence of DAEFRHDSGYEVHHQKLVFFAEHRWC-CPGCCKTFGAIIGLMVGGVV.

23. A method for producing a peptide probe comprising the steps of:
a) lyophilizing a peptide probe;
b) solubilizing the lyophilized peptide probe of step a) with 1,1,1,3,3,3-hexafluoro-2-propanol at 1 mg peptide probe per 2 mL 1,1,1,3,3,3-hexafluoro-2-propanol for 3 hours;
c) aliquoting the solubilized peptide probe of step b) into 20 vials containing 0.05 mg peptide probe each;
d) lyophilizing the aliquoted peptide probe of step c);
e) solubilizing the lyophilized peptide probe of step d) with dimethyl sulfoxide containing 10 mM 2-mercaptoethanol at 0.05 mg peptide probe per 0.01 mL dimethyl sulfoxide containing 10 mM 2-mercaptoethanol for 1 hour; and then
f) diluting the peptide probe of step e) by 100-fold into an aqueous buffer containing Aβ, wherein the peptide probe of step e) has a mass or molar concentration that is decreased by 100-fold after dilution.

24. The method as claimed in claim 23, wherein the peptide probe is PG46 having the amino acid sequence of DAEFRHDSGYEVHHQKLVFFAEHRWCCPGCCKTFGAIIGLMVGGVV.

* * * * *

SEQUENCE LISTING

<160> NUMBER OF SEQ ID NOS: 7

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Leu Val Phe Phe Lys Lys Lys Lys Lys Lys
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: A non-cysteine amino acid

<400> SEQUENCE: 2

Cys Cys Xaa Xaa Cys Cys
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Cys Pro Gly Cys Cys
1               5

<210> SEQ ID NO 4
<211> LENGTH: 46
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 4

Asp Ala Glu Phe Arg His Asp Ser Gly Tyr Glu Val His His Gln Lys
1               5                   10                  15

Leu Val Phe Phe Ala Glu His Arg Trp Cys Cys Pro Gly Cys Cys Lys
            20                  25                  30

Thr Phe Gly Ala Ile Ile Gly Leu Met Val Gly Gly Val Val
        35                  40                  45

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      probe

<400> SEQUENCE: 5

```
Asp Ala Glu Phe Arg His Asp Ser Gly Tyr Glu Val His His Gln Lys
1               5                   10                  15

Leu Val Phe Phe Ala Glu Cys Cys Pro Gly Cys Cys Gly Ala Ile Ile
            20                  25                  30

Gly Leu Met Val Gly Gly
        35

<210> SEQ ID NO 6
<211> LENGTH: 40
<212> TYPE: PRT
<213> ORGANISM: Unknown
<220> FEATURE:
<223> OTHER INFORMATION: Description of Unknown: Beta amyloid
      polypeptide

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 7
<211> LENGTH: 42
<212> TYPE: PRT
<213> ORGANISM: Unknown
<220> FEATURE:
<223> OTHER INFORMATION: Description of Unknown: Beta amyloid
      polypeptide

<400> SEQUENCE: 7

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```